United States Patent
Fischer et al.

(10) Patent No.: US 6,433,192 B1
(45) Date of Patent: Aug. 13, 2002

(54) METHOD FOR PRODUCING MIXTURES OF 1,4-BUTANEDIOL, TETRAHYDROFURAN AND γ-BUTYROLACTONE

(75) Inventors: Rolf Fischer, Heidelberg; Gerd Kaibel, Lampertheim; Rolf Pinkos, Bad Dürkheim; Ralf-Thomas Rahn, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/673,847

(22) PCT Filed: Apr. 21, 1999

(86) PCT No.: PCT/EP99/02685

§ 371 (c)(1),
(2), (4) Date: Jun. 4, 2001

(87) PCT Pub. No.: WO99/55654

PCT Pub. Date: Nov. 4, 1999

(30) Foreign Application Priority Data

Apr. 23, 1998 (DE) .......................................... 198 18 340

(51) Int. Cl.$^7$ .................... C07D 307/02; C07D 407/00; C07C 31/18
(52) U.S. Cl. ...................... 549/295; 549/429; 568/854; 568/853
(58) Field of Search ............................... 568/854, 853; 549/295, 429

(56) References Cited

U.S. PATENT DOCUMENTS

| | | | |
|---|---|---|---|
| 4,361,710 A | 11/1982 | Weitz et al. | 568/864 |
| 4,562,283 A | 12/1985 | Schnabel et al. | 560/204 |
| 5,981,810 A * | 11/1999 | Okuyama | 568/868 |
| 6,274,743 B1 * | 8/2001 | Tuck et al. | 549/295 |
| 6,297,389 B1 * | 10/2001 | Castiglioni et al. | 549/295 |
| 6,350,924 B1 * | 2/2002 | Fischer et al. | 568/864 |

FOREIGN PATENT DOCUMENTS

| | | |
|---|---|---|
| DE | 31 06 819 | 9/1982 |
| EP | 149 144 | 7/1985 |
| EP | 206 194 | 12/1986 |
| EP | 212 121 | 3/1987 |

* cited by examiner

*Primary Examiner*—Deborah C. Lambkin
(74) *Attorney, Agent, or Firm*—Keil & Weinkauf

(57) ABSTRACT

In a process for preparing 1,4-butanediol, tetrahydrofuran and γ-butyrolactone by oxidation of butane to give a product stream comprising maleic anhydride, absorption of maleic anhydride from the product stream using a high-boiling alcohol to give a liquid absorption product comprising monoesters and diesters of maleic acid and also high-boiling alcohol, after-esterification of the liquid absorption product and subsequent hydrogenation of the after-esterified product in the liquid phase, the high-boiling alcohol is a polyhydric alcohol having a boiling point at atmospheric pressure of above 233° C. and the after-esterified product has an acid number of less than 30 mg KOH/g and a water content of less than 1% by weight.

10 Claims, No Drawings

METHOD FOR PRODUCING MIXTURES OF 1,4-BUTANEDIOL, TETRAHYDROFURAN AND γ-BUTYROLACTONE

This application is a 371 of PCT/EP99/02685 filed Apr. 21, 1999.

The present invention relates to a process for preparing mixtures comprising 1,4-butanediol, tetrahydrofuran (THF) and γ-butyrolactone (GBL) from the product gas stream from a reactor for the oxidation of butane by a) absorption of maleic anhydride (MA) from the product gas stream using a high-boiling alcohol, b) conversion of the maleic monoester formed into the maleic diester and c) hydrogenation of the latter in the liquid phase.

Numerous processes for converting MA into the corresponding monoesters and diesters and hydrogenating the latter are known.

EP-B 0 149 144, EP-B 0 206 194 and EP-B 0 212 121 describe processes for the continuous separation of MA from gaseous reaction mixtures which are obtained in the catalytic oxidation of hydrocarbons. Here, the MA-containing, gaseous reaction mixture is brought into contact with a monohydric alcohol. The gaseous materials formed are brought into contact with dicarboxylic diesters (EP-B 0 206 194 dibutyl fumarate or succinate, EP B 0 212 121 diesters of fumaric, succinic or maleic acid, EP-B 0 149 144 dibutyl maleate) in a countercurrent process and the liquid process product is taken off at the bottom. The liquid process product comprises predominantly the corresponding monoalkyl and dialkyl esters of maleic acid. These are heated at from 110° C. to 200° C. to complete the esterification and then provide a suitable starting material for the hydrogenation to form 1,4-butanediol.

A disadvantage of this process is that, apart from the alcohol, an additional material (dicarboxylic diester) which transfers the gaseous reaction products formed from alcohol and MA into the liquid phase is circulated. This must not be hydrogenated in a hydrogenation, so that it is always only possible to achieve incomplete conversion, which means complicated control of the hydrogenation. Furthermore, the dibutyl ester of a dicarboxylic acid used as absorption medium has to be separated from butanediol when the product is worked up by distillation, which complicates the work-up.

DE-A 31 06 819, too, describes a process for preparing 1,4-butanediol by catalytic hydrogenation of a mixture which is obtained by treatment of MA-containing, gaseous reaction mixtures with aliphatic alcohols. The absorption of the MA is carried out using monohydric or dihydric alcohols having boiling points above 180° C. An additional absorption medium is not necessary. The subsequent after-esterification of the absorption product is carried out at from 120° C. to 150° C. The diester-containing stream is finally catalytically hydrogenated, but the space-time yield (0.04 kg of butanediol/liter×hour) is low since the acid number after the after-esterification is too high.

Although the abovementioned processes can be carried out industrially, they have disadvantages which lead to high production costs. These disadvantages are, in particular, complicated control of the hydrogenation and a low space-time yield in the catalytic hydrogenation.

It is an object of the present invention to provide a process which requires very little absorption medium, achieves a good space-time yield in the catalytic hydrogenation using inexpensive catalysts and, in the separation of the desired products, forms no mixtures which are difficult to separate.

We have found that this object is achieved by a process for preparing 1,4-butanediol, tetrahydrofuran (THF) and γ-butyrolactone (GBL) by oxidation of butane to give a product stream comprising maleic anhydride, absorption of maleic anhydride from the product stream using a high-boiling alcohol to give a liquid absorption product comprising monoesters and diesters of maleic acid and also high-boiling alcohol, after-esterification of the liquid absorption product and subsequent hydrogenation of the after-esterified product in the liquid phase. In the process of the present invention, the high-boiling alcohol is a polyhydric alcohol having a boiling point at atmospheric pressure of above 233° C. and the after-esterified product has an acid number of less than 30 mg KOH/g and a water content of less than 1% by weight.

In the context of the present invention, absorption means the separation of MA from a product stream obtained by oxidation of butane using a high-boiling alcohol to carry out this separation. In this absorption step, the MA reacts with the alcohol to give a maleic monoester which constitutes the main product in the absorption product.

In this process, a liquid process product is obtained directly by addition of the esterifying alcohol under the prevailing reaction conditions. The additional use of a high-boiling absorption medium such as a diester of a dicarboxylic acid is not necessary. By this means, a complicated, later separation of the desired products is avoided. Owing to the low acid number, the hydrogenation can be carried out using inexpensive catalysts and in good yields using the after-esterified product. This allows cost savings.

Catalytic oxidation of butane or another hydrocarbon in the gas phase over a vanadium pentoxide catalyst activated with, for example, $MoO_3$ gives a product stream comprising MA and by-products such as carbon dioxide, acetic acid and acrylic acid. In the process of the present invention, this MA-containing, gaseous product stream is brought into contact with a high-boiling alcohol to absorb the MA. In an advantageous embodiment of the invention, the reaction gas is fed in below the surface of the liquid, high-boiling alcohol, e.g. through an immersed tube. Preference is given to a process in which the reaction mixture is introduced directly from below into an absorption column in which the liquid, high-boiling alcohol flows toward the reaction mixture. Carrying out the MA absorption in a column or a plurality of columns connected in series is preferred.

Suitable columns are, for example, bubble cap tray columns, columns containing units of packing or columns packed with loose packing elements, with preference being given to using the latter. These can be provided with intermediate coolers in order to remove the heat of absorption.

The MA content of the product stream from the butane oxidation is not critical for the process of the present invention. In customary processes, it is in the range from 0.5 to 2% by volume. The temperature of the product gas stream is likewise generally not critical. It should, if possible, be not below the dew points and melting points of the individual components in order to avoid caking, i.e. it should preferably be at least 100° C.

The by-products occurring in the oxidation of butane, for example $CO_2$, acetic acid and acrylic acid, are likewise not critical for the process. They are either mostly carried away with the waste gas stream or go into the absorption medium. If they do not react with the esterifying alcohol, they are removed in the thermal treatment of the liquid absorption product (partly with the water).

Alcohols used in the process of the present invention are polyhydric alcohols having a boiling point at atmospheric pressure of above 233° C., preferably above 250° C. As polyhydric alcohols preference is given to using dihydric to tetrahydric alcohols, particularly preferably dihydric alcohols (diols). Examples of alcohols used are polyethylene glycols, α,ω-diols and cyclohexanedimethanols, e.g. 1,5-pentanediol, 1,6-hexanediol, 1,7-heptanediol, 1,8-octanediol, 1,12-dodecanediol, 1,4-cyclohexanedimethanol, 1,3-cyclohexanedimethanol, trimethylolpropane, neopentyl glycol, triethylene glycol, tetraethylene glycol and pentaethylene glycol, very particularly preferably 1,6-hexanediol and 1,4-cyclohexanedimethanol. As trihydric alcohol, it is possible to use glycerol; as tetrahydric alcohol, pentaerythritol. The alcohols can be used in pure form or as mixtures of various alcohols.

In general, the alcohol is used in a molar excess over the MA of up to 30, preferably up to 15, very particularly preferably up to 5.

In the absorption, a monoester of maleic acid is first formed from the MA and the alcohol. This monoester is high-boiling and thus no longer volatile at the reaction temperatures. The absorption can be carried out so that the after-esterification of the monoester to form the diester also takes place in the apparatus used for the absorption of MA. In this reaction, the monoester can react with further free alcohol or with another monoester molecule. The water eliminated in the reaction can, if the temperatures are high enough, be removed with the waste gas stream.

If relatively large amounts of monoester are still present in the liquid product, preference is given to carrying out a thermal after-esterification in a residence time vessel and thus completing the esterification to form the diester. The after-esterification can be carried out with or without addition of an esterification catalyst.

Esterification catalysts which can be used are, in principle, all homogeneous or heterogeneous catalysts known for the esterification of acids. Preference is given to heterogeneous catalysts such as $TiO_2$, $ZrO_2$, $Al_2O_3$, $SiO_2$, silicates, zeolites, heteropolyacids or acid ion exchangers.

Particular preference is given to carrying out the esterification without catalyst, purely thermally. The monoester-containing stream is then after-esterified at temperatures of from 160° C. to 300° C. in general, preferably from 160° C. to 250° C., particularly preferably from 180° C. to 240° C. The water of reaction is generally removed continuously by distillation. The residence time usually is a maximum of 3 hours, in general from 0.1 to 3 hours, preferably from 0.2 to 2.5 hours, particularly preferably from 0.3 to 2 hours. To remove the water of reaction, it is also possible to carry out the after-esterification in a stripping column and remove the water liberated as water vapor by means of stripping gas. It is also possible to apply a vacuum to make it easier to remove the water of reaction. Another possibility is to add entrainers for water, e.g. aromatic hydrocarbons. The water content after the esterification is less than 1% by weight, preferably less than 0.5%, particularly preferably less than 0.2%.

Owing to the choice of esterification conditions, the free acid content of the esterification product is low. The free acid content (measured by titration) before the hydrogenation is less than 30 mg KOH/g, preferably less than 20 mg KOH/g, particularly preferably less than 10 mg KOH/g.

The hydrogenation can be carried out in the presence of an inert organic solvent, particularly if only small quantities are to be hydrogenated. For example, the esterification product can be diluted with an inert organic solvent, preferably ethylene glycol dimethyl ether, to make it more pumpable. When carrying out the reaction industrially, an additional solvent is generally dispensed with.

The hydrogenation is carried out batchwise or continuously in the liquid phase over fixed-bed or suspended or homogeneous, soluble catalysts. Preference is given to a continuous procedure. In the case of fixed-bed catalysts, hydrogenation can be carried out in the downflow or upflow mode, with or without product recirculation. One or more reactors can be operated in series or in parallel. For example, it is possible to hydrogenate predominantly the C—C double bond of the maleic esters in the first reactor, forming succinic esters, and subsequently to continue the hydrogenation in a second reactor to give butanediol, THF and GBL.

The hydrogenation is carried out generally at temperatures of from 70° C. to 350° C., preferably from 80° C. to 300° C., particularly preferably from 80° C. to 260° C., and at pressures of from 20 bar to 350 bar, preferably from 40 bar to 320 bar in general, particularly preferably from 60 bar to 300 bar.

Hydrogenation catalysts which can be used in the process of the invention are, in general, heterogeneous or homogeneous catalysts suitable for the hydrogenation of carbonyl groups. Preference is given to heterogeneous catalysts. Examples are described in Houben-Weyl, Methoden der Organischen Chemie, Volume IV/1c, pp. 16 to 26, Georg Thieme Verlag, 1980.

Among these hydrogenation catalysts, preference is given to those which comprise at least one element of groups Ib, VIb, VIIb and VIII, and IIIa, IVa and Va of the Periodic Table of the Elements, in particular copper, chromium, rhenium, cobalt, rhodium, nickel, palladium, iron, platinum, indium, tin and antimony. Particular preference is given to catalysts comprising copper, cobalt, palladium, platinum or rhenium. Among these, very particular preference is given to those which comprise copper.

One example of a type of catalyst which can be used for the process of the present invention are unsupported catalysts. In these, the catalytically active metals are present essentially without support materials. Examples are the Raney catalysts, e.g. those based on Ni, Cu or cobalt. Other examples are Pd black, Pt black, Cu sponge, alloys or mixtures of, for example, Pd/Re, Pt/Re, Pd/Ni, Pd/Co or Pd/Re/Ag.

The catalysts used in the process of the present invention can also be precipitated catalysts. Such catalysts can be prepared by precipitating their catalytically active components from their salt solutions, in particular from their nitrate and/or acetate solutions, for example by addition of alkali metal hydroxide and/or alkaline earth metal hydroxide and/or carbonate solutions, e.g. as sparingly soluble hydroxides, hydrated oxides, basic salts or carbonates. The precipitates obtained are subsequently dried and then converted into the corresponding oxides, mixed oxides and/or mixed-valence oxides by calcination at generally from 300 to 700° C., preferably from 400 to 600° C. These oxides are reduced by treatment with hydrogen or hydrogen-containing gases at generally from 50 to 700° C., preferably from 100 to 400° C., to give the corresponding metals and/or oxidic compounds of lower oxidation states and thus converted into the actual catalytically active form. The reduction is generally carried out until no more water is formed.

In the preparation of precipitated catalysts which comprise a support material, the precipitation of the catalytically active components can be carried out in the presence of the support material concerned. The catalytically active components can also be advantageously precipitated simultaneously with the support material from the salt solutions concerned.

In the process of the present invention, preference is given to using hydrogenation catalysts which comprise the metals or metal compounds which catalyze the hydrogenation deposited on a support material. Apart from the abovementioned precipitated catalysts, which comprise a support material in addition to the catalytically active components, support materials in general in which the hydrogenation-active catalytic components have been applied to a support material by, for example, impregnation are also suitable for the process of the present invention.

The method by which the catalytically active metals are applied to the support is generally not critical and the application can be carried out in various ways. The catalytically active metals can be applied to these support materials by, for example, impregnation with solutions or suspensions of the salts or oxides of the elements concerned, drying and subsequent reduction of the metal compounds to the corresponding metals or compounds of lower oxidation states by means of a reducing agent, preferably using hydrogen or complex hydrides.

Another possible way of applying the catalytically active metals to the supports is to impregnate the supports with solutions of salts which are readily decomposed thermally, e.g. nitrates, or complexes which are readily decomposed thermally, e.g. carbonyl or hydrido complexes, of the catalytically active metals and to heat the support which has been impregnated in this way at from 300 to 600° C. so as to effect thermal decomposition of the adsorbed metal compounds. This thermal decomposition is preferably carried out under a protective gas atmosphere. Suitable protective gases are, for example, nitrogen, carbon dioxide, hydrogen or the noble gases.

The catalytically active metals can also be deposited on the catalyst support by vapor deposition or by flame spraying.

The content of the catalytically active metals in the supported catalysts is in principle not critical for the success of the process of the present invention. Higher contents of catalytically active metals in the supported catalysts generally lead to higher space-time yields than lower contents.

In general, use is made of supported catalysts whose content of catalytically active metals is from 0.1 to 90% by weight, preferably from 0.5 to 40% by weight, based on the total catalyst. Since these content figures are based on the total catalyst including support materials but the different support materials have very different densities and specific surface areas, it is possible for the contents to be above or below the ranges specified without this having an adverse effect on the result of the process of the present invention.

It is also possible for a plurality of catalytically active metals to be applied to the respective support material.

Furthermore, the catalytically active metals can be applied to the support by, for example, the methods described in DE-A 25 19 817, EP-A 0 147 219 and EP-A 0 285 420. In the catalysts described in these documents, the catalytically active metals are present as alloys. These are produced, for example, by impregnation with a salt or complex of the abovementioned metals and subsequent thermal treatment and/or reduction.

The activation of both the precipitated catalysts and the supported catalysts can also be carried out in situ at the beginning of the reaction by means of the hydrogen present, but these catalysts are preferably activated separately before use.

Support materials which can be used are, in general, the oxides of aluminum and titanium, zirconium dioxide, silicon dioxide, clay minerals, e.g. montmorillonites, silicates such as magnesium or aluminum silicates, zeolites such as ZSM-5 or ZSM-10 zeolites, and activated carbon. Preferred support materials are aluminum oxides, titanium dioxide, silicon dioxide, zirconium dioxide and activated carbon. Mixtures of various support materials can also serve as support for the catalysts to be used in the process of the present invention.

Examples of heterogeneous catalysts which can be used in the process of the present invention are: cobalt on activated carbon, cobalt on silicon dioxide, cobalt on aluminum oxide, rhenium on activated carbon, rhenium on silicon dioxide, rhenium/tin on activated carbon, rhenium/platinum on activated carbon, copper on activated carbon, copper/silicon dioxide, copper/aluminum oxide, copper chromite, barium copper chromite, copper/aluminum oxide/manganese oxide, copper/aluminum oxide/zinc oxide and the catalysts described in DE-A 39 32 332, U.S. Pat. No. 3 449 445, EP-A 0 044 444, EP-A 0 147 219, DE-A 39 04 083, DE-A 23 21 101, EP-A 0 415 202, DE-A 23 66 264, EP-A 0 552 463 and EP-A 0 100 406.

Preferred catalysts comprise at least one of the metals copper, manganese, rhenium, cobalt, chromium, palladium, platinum or nickel. Particular preference is given to copper, cobalt, palladium, platinum or rhenium.

The ratio of the individual desired products present in the hydrogenation product, viz. 1,4-butanediol, THF and GBL, can vary. For example, the molar ratio of the products may be: butanediol 50–95 mol %, THF 2–40 mol %, GBL 0.1–20 mol %, where the sum of the mole fractions of 1,4-butanediol, THF and GBL is 100 mol %. The ratio of the desired products is determined predominantly by the parameters pressure, temperature, residence time and catalyst in the hydrogenation. Thus, for example, the GBL content can be reduced to virtually 0 if the hydrogenation is carried out at a high pressure, a low temperature and a long residence time. The THF content can be high when the hydrogenation catalyst has acid centers.

Further products which are or can be present in the hydrogenation product are, for example, water, n-butanol, n-propanol and esters of succinic acid and also the absorption alcohol. The alcohol components of the succinic esters can be both the previously used absorption alcohol and butanediol. The succinic esters can be recirculated together with the absorption alcohol.

The work-up of the reaction products can be carried out in a manner with which those skilled in the art are familiar. Preference is given to a work-up by distillation. Here, for example, low boilers such as THF and any water, butanol or propanol present can first be taken off at the top of a distillation column and the remaining products butanediol and GBL can then be distilled off from the bottoms. The bottoms, which consist predominantly of the absorption alcohol, are subsequently recirculated to the MA absorption. If desired, a small bleed stream can be discharged.

The following examples illustrate the invention.

EXAMPLE 1

A product gas stream from an n-butane oxidation, which comprised about 1% by volume of MA and 99% by volume of air, was passed at 100° C. into the lower part of a packed column which had about 25 theoretical plates and was provided with intermediate coolers to remove the heat of absorption. The intermediate coolers were held at about 65° C. 1,4-Cyclohexanedimethanol at 70° C. was pumped to the top of the column. A temperature of 87° C. was established at the top of the column and a temperature of 105° C. was established at the bottom of the column.

Overall, about 25 g of MA were bound by 144 g of 1,4-cyclohexanedimethanol. The absorption product was subsequently heated at 200° C. for 2.5 hours and then at 225° C. for another 30 minutes in a residence time vessel. The water of esterification was distilled off during this procedure. The product then contained 0.19% by weight of water and the acid number was 19.1 mg KOH/g. To improve the pumpability, the product was diluted with the same amount of ethylene glycol dimethyl ether and was hydrogenated continuously over 25 ml of a Cu catalyst from Süd-Chemie AG, Munich (T 4489) at 220° C. and 220 bar (feed=about 20 g/h, tube reactor, downflow mode without product recirculation).

The colorless hydrogenation product comprised, excluding cyclohexanedimethanol and ethylene glycol dimethyl ether, 70 mol % of 1,4-butanediol, 10 mol % of THF and less than 1 mol % of GBL. The remainder was predominantly n-butanol and diesters of succinic acid. The product was worked up by distillation, with THF, butanol, ethylene glycol dimethyl ether, GBL and 1,4-butanediol being distilled off. The bottoms consisted predominantly of cyclohexanedimethanol and diesters of succinic acid.

EXAMPLE 2

Using a method analogous to Example 1, MA was absorbed in 1,6-hexanediol. Here, 73.5 g of MA were reacted with 177 g of hexanediol. The after-esterification was carried out for 1 hour at 200° C and 225° C. The esterification product contained 0.27% by weight of water and had an acid number of 8.3 mg KOH/g. The product was diluted with ethylene glycol dimethyl ether as described in Example 1 before the hydrogenation and the hydrogenation was carried out as in Example 1 but this time at 220 bar or 110 bar. At 220 bar, the colorless hydrogenation product comprised, excluding hexanediol and ethylene glycol dimethyl ether, 85 mol % of 1,4-butanediol, 3 mol % of THF and about 0.2 mol % of GBL. The remainder was predominantly butanol and diesters of succinic acid.

At 110 bar, the colorless hydrogenation product comprised, excluding hexanediol and ethylene glycol dimethyl ether, 68 mol % of 1,4-butanediol, 2 mol % of THF and 8 mol % of GBL. The remainder was predominantly butanol and diesters of succinic acid.

Comparative Example C1
(DE-A 31 06 819)

Using a method analogous to Example 2, MA was reacted with hexanediol, but the esterification was carried out for 3 hours at 150° C. The esterification product had a water content of 0.2% and an acid number of 49 mg KOH/g. The hydrogenation was carried out at 110 bar as described in Example 2. After only a short time, the previously colorless hydrogenation product became reddish brown (copper/manganese) and the hydrogenation activity dropped.

We claim:

1. A process for preparing 1,4-butanediol, tetrahydrofuran and γ-butyrolactone by oxidation of butane to give a product stream comprising maleic anhydride, absorption of maleic anhydride from the product stream using a high-boiling alcohol to give a liquid absorption product comprising monoesters and diesters of maleic acid and also high-boiling alcohol, after-esterification of the liquid absorption product and subsequent hydrogenation of the after-esterified product in the liquid phase, wherein the high-boiling alcohol is a polyhydric alcohol having a boiling point at atmospheric pressure of above 233° C. and the after-esterified product has an acid number of less than 30 mg KOH/g and a water content of less than 1% by weight.

2. A process as claimed in claim 1, wherein the alcohol used is 1,6-hexanediol or 1,4-cyclohexanedimethanol.

3. A process as claimed in claim 1, wherein the after-esterification is carried out in the apparatus used for the absorption of maleic anhydride.

4. A process as claimed in claim 1, wherein the after-esterification is carried out at from 160° C. to 300° C.

5. A process as claimed in claim 1, wherein the after-esterification is carried out at a residence time of not more than 3 hours.

6. A process as claimed in claim 1, wherein the hydrogenation is carried out at from 70° C. to 350° C. and at a pressure of from 20 to 350 bar.

7. A process as claimed in claim 1, wherein the hydrogenation is carried out in the presence of a catalyst comprising at least one element of groups Ib, VIb, VIIb and VIIIb of the Periodic Table of the Elements.

8. A process as claimed in claim 7, wherein the hydrogenation catalyst comprises copper.

9. A process as claimed in claim 1, wherein the ratio of the individual desired products in the hydrogenation product, viz. 1,4-butanediol, tetrahydrofuran and γ-butyrolactone, is 50–95 mol % of 1,4-butanediol, 2–40 mol % of tetrahydrofuran and 0.1–20 mol % of γ-butyrolactone, where the sum of the mole fractions of 1,4-butanediol, tetrahydrofuran and γ-butyrolactone is 100 mol %.

10. A process as claimed claim 1, wherein the high-boiling alcohol is returned to the absorption after the hydrogenation.

* * * * *